US007472593B2

(12) United States Patent
Tenney

(10) Patent No.: US 7,472,593 B2
(45) Date of Patent: Jan. 6, 2009

(54) FLUID LEVEL REGULATOR

(75) Inventor: Douglas A. Tenney, North Reading, MA (US)

(73) Assignee: CYTYC Corporation, Marlborough, MA (US)

( * ) Notice: Subject to any disclaimer, the term of this patent is extended or adjusted under 35 U.S.C. 154(b) by 298 days.

(21) Appl. No.: 11/292,840

(22) Filed: Dec. 1, 2005

(65) Prior Publication Data

US 2007/0125170 A1 Jun. 7, 2007

(51) Int. Cl.
*G01F 23/00* (2006.01)

(52) U.S. Cl. ............... 73/290 R; 73/290 V; 73/293; 73/299; 73/302; 73/327

(58) Field of Classification Search ........... 73/290 R, 73/290 V, 290 B, 293, 327, 299, 302
See application file for complete search history.

(56) References Cited

U.S. PATENT DOCUMENTS

| 3,661,191 | A | * | 5/1972 | Harley et al. ............ 141/41 |
| 4,944,336 | A | * | 7/1990 | Stembridge et al. ....... 141/95 |
| 5,021,665 | A | * | 6/1991 | Ames .................. 250/357.1 |
| 5,143,627 | A | | 9/1992 | Lapidus et al. |
| 5,364,597 | A | | 11/1994 | Polk, Jr. et al. |
| 5,772,818 | A | | 6/1998 | Polk, Jr. et al. |
| 6,318,190 | B1 | | 11/2001 | Radcliffe et al. |
| 6,324,906 | B1 | * | 12/2001 | Rinkewich et al. ........ 73/219 |
| 6,443,022 | B1 | * | 9/2002 | Gordon ................ 73/864.25 |
| 6,448,573 | B1 | * | 9/2002 | Benton .................. 250/577 |
| 6,572,824 | B1 | | 6/2003 | Ostgaard et al. |
| 6,664,558 | B1 | * | 12/2003 | Barbier .................. 250/577 |
| 6,748,803 | B1 | * | 6/2004 | Durkee et al. ............. 73/290 V |

(Continued)

FOREIGN PATENT DOCUMENTS

| EP | 0448837 | 10/1991 |
| JP | 10197538 | 7/1998 |

OTHER PUBLICATIONS

PCT International Search Report for PCT/US2006/061012, Applicant CYTYC Corp., Forms PCT/ISA/210 and 220, dated Oct. 30, 2007 (5 pages).

(Continued)

*Primary Examiner*—Hezron Williams
*Assistant Examiner*—Gunnar J Gissel
(74) *Attorney, Agent, or Firm*—Vista IP Law Group, LLP

(57) ABSTRACT

A biological specimen collection and transfer system, comprises a biological sample container configured for storing a biological fluid sample, and a fluid level regulator configured to determine a fluid level in the biological sample container and to dispense a fluid into the container if the determined fluid level is less than a desired fluid level. A method of regulating a fluid level of a biological fluid sample in a container during a process of transferring biological matter in the fluid sample to a specimen slide, the method comprises monitoring a pressure of an interior chamber of a specimen filter, the chamber coupled to a vacuum source and having one end submerged in the fluid sample, determining a fluid level of the fluid sample in the container based on a detected change in pressure of the specimen filter chamber, and adding a liquid to the container if the determined fluid level is less than a desired fluid level.

9 Claims, 13 Drawing Sheets

U.S. PATENT DOCUMENTS

| | | | |
|---|---|---|---|
| 6,931,925 B2 * | 8/2005 | Huemer et al. ................. | 73/299 |
| 6,951,131 B2 * | 10/2005 | Sawert et al. ............. | 73/290 V |
| 2002/0000120 A1 * | 1/2002 | Dillon ......................... | 73/327 |
| 2004/0069714 A1 | 4/2004 | Ferguson | |
| 2005/0092080 A1 * | 5/2005 | Harazin et al. ............ | 73/290 R |
| 2006/0123901 A1 * | 6/2006 | Ramus et al. ............. | 73/290 R |

OTHER PUBLICATIONS

PCT Written Opinion of the International Search Authority for PCT/US2006/061012, Applicant CYTYC Corp., Form PCT/ISA/237, dated Oct. 30, 2007 (6 pages).

* cited by examiner

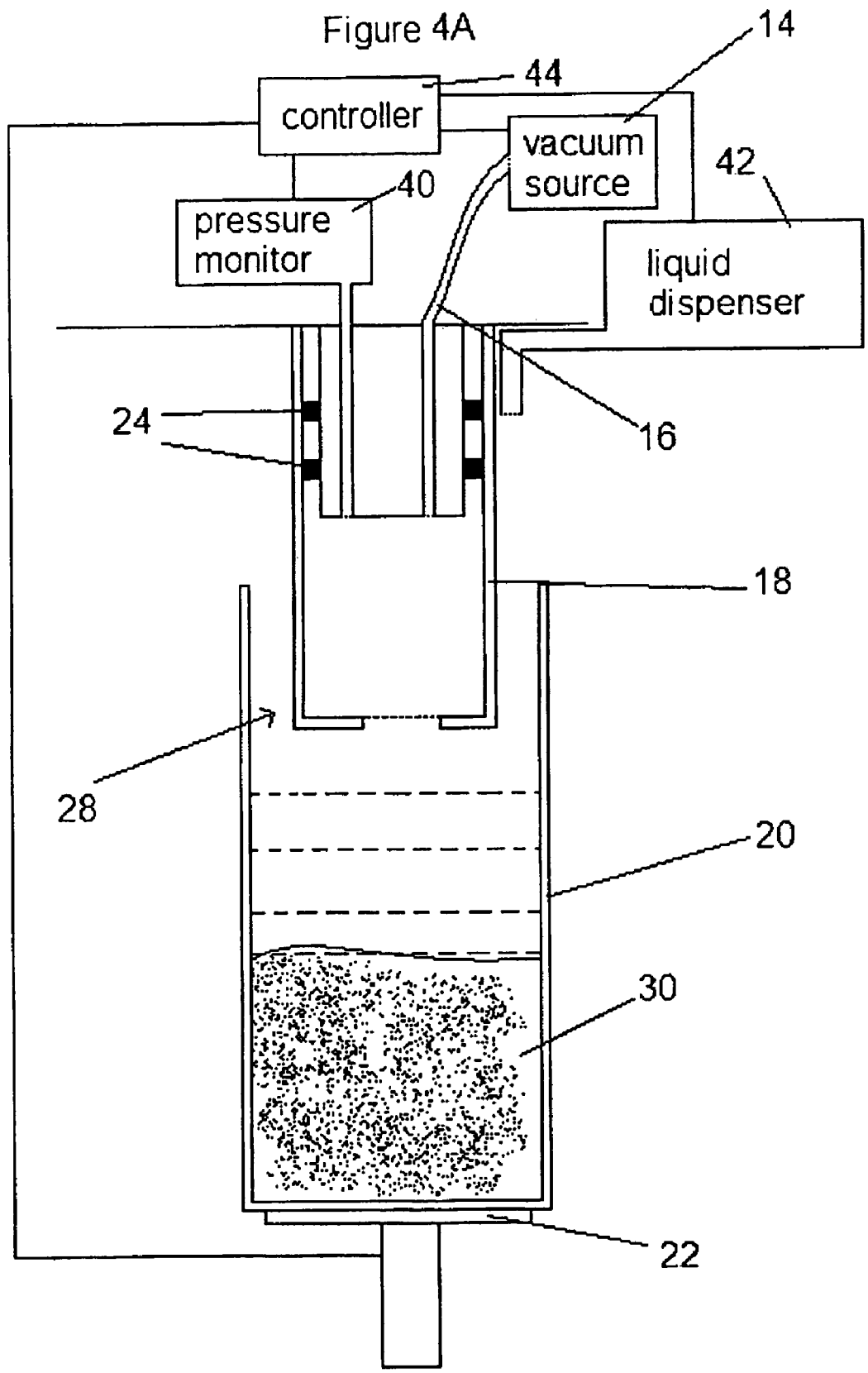

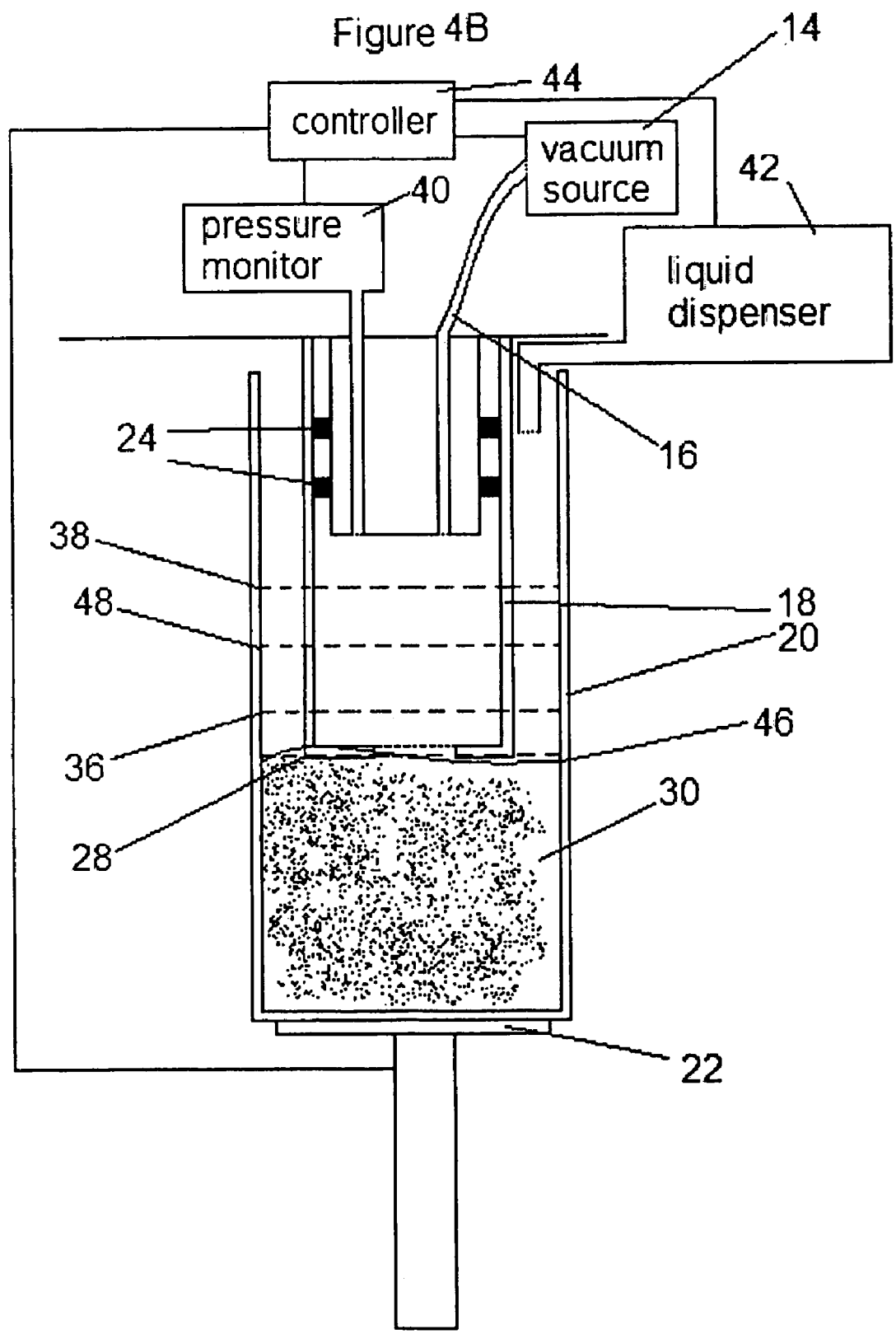

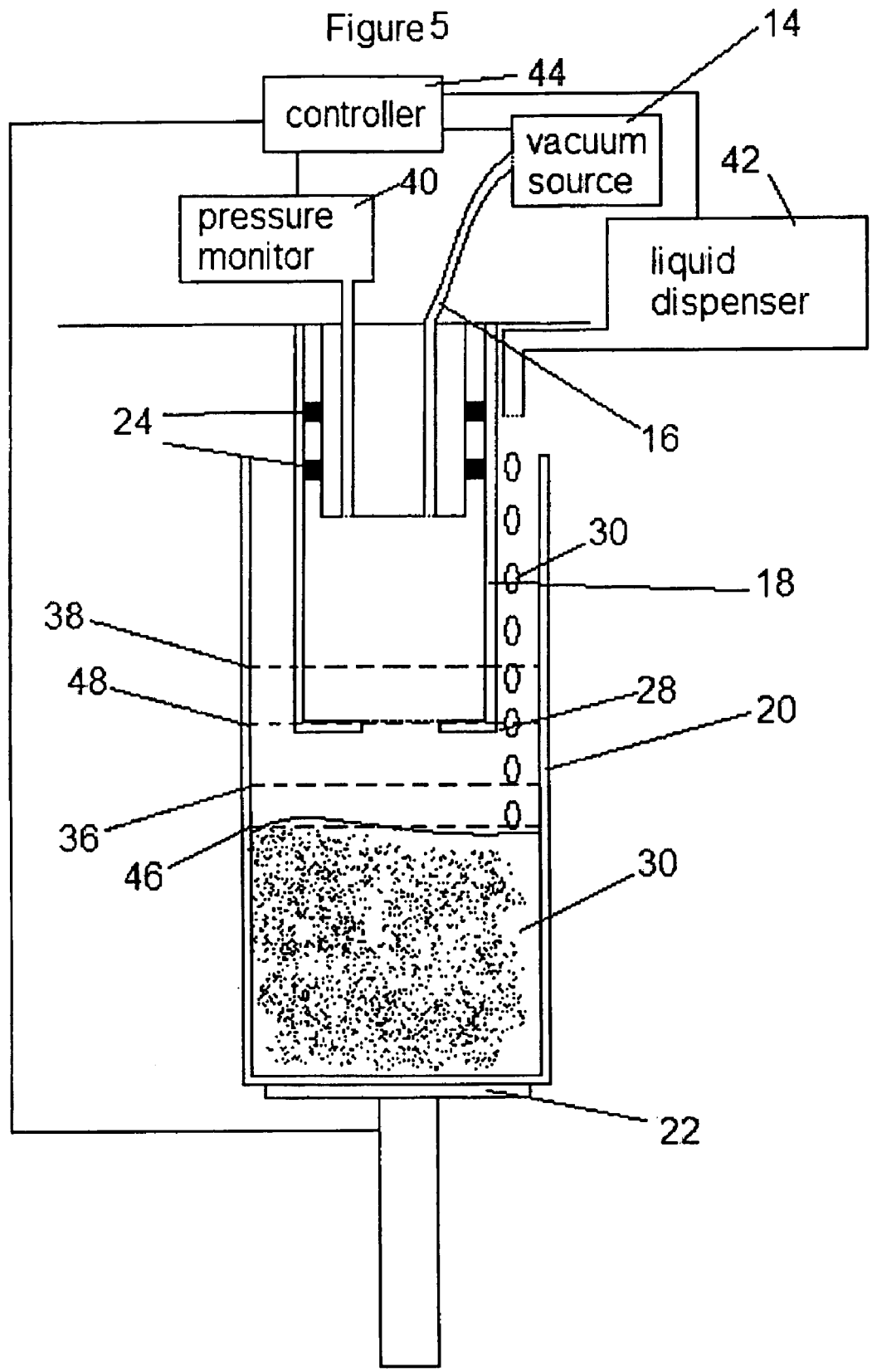

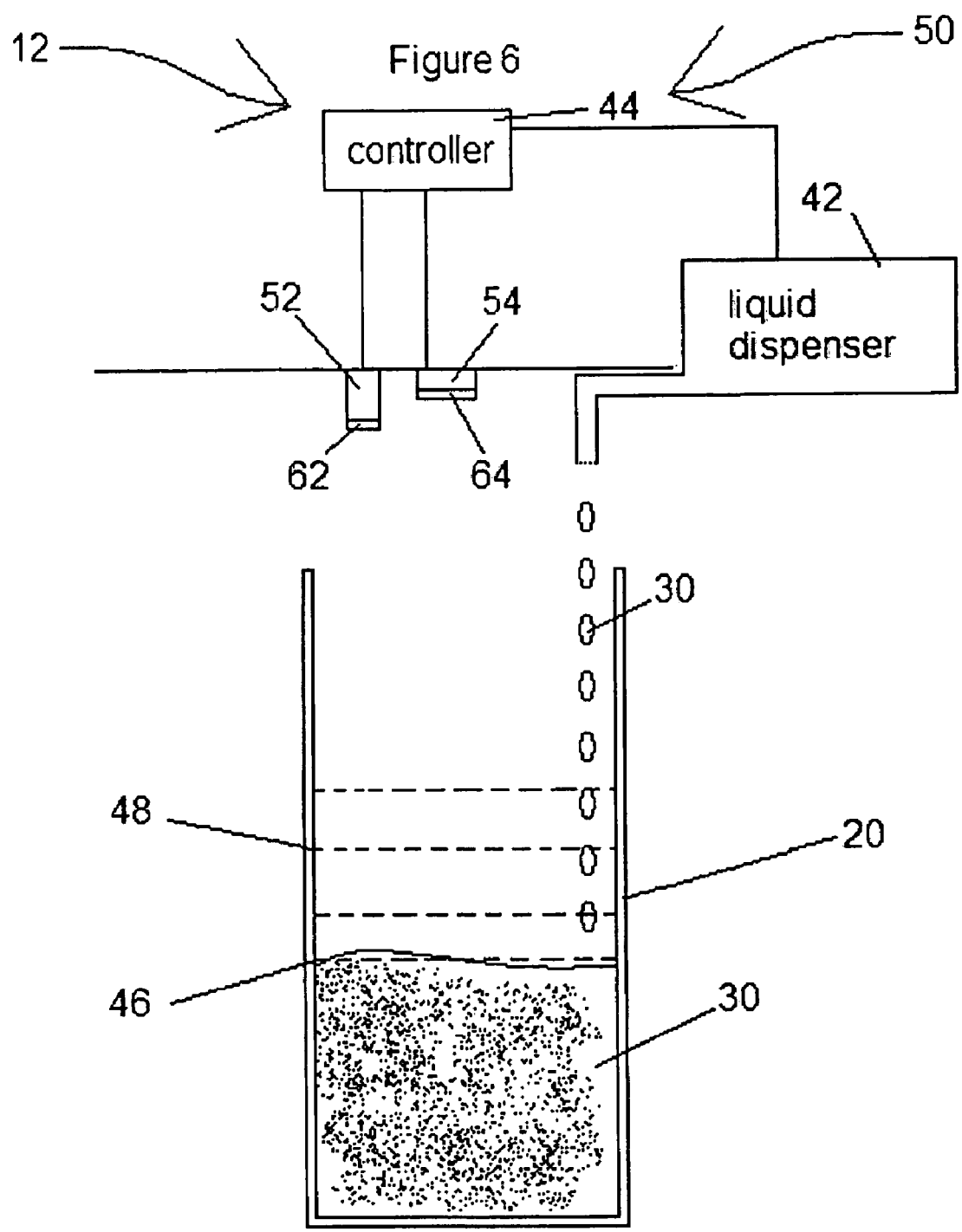

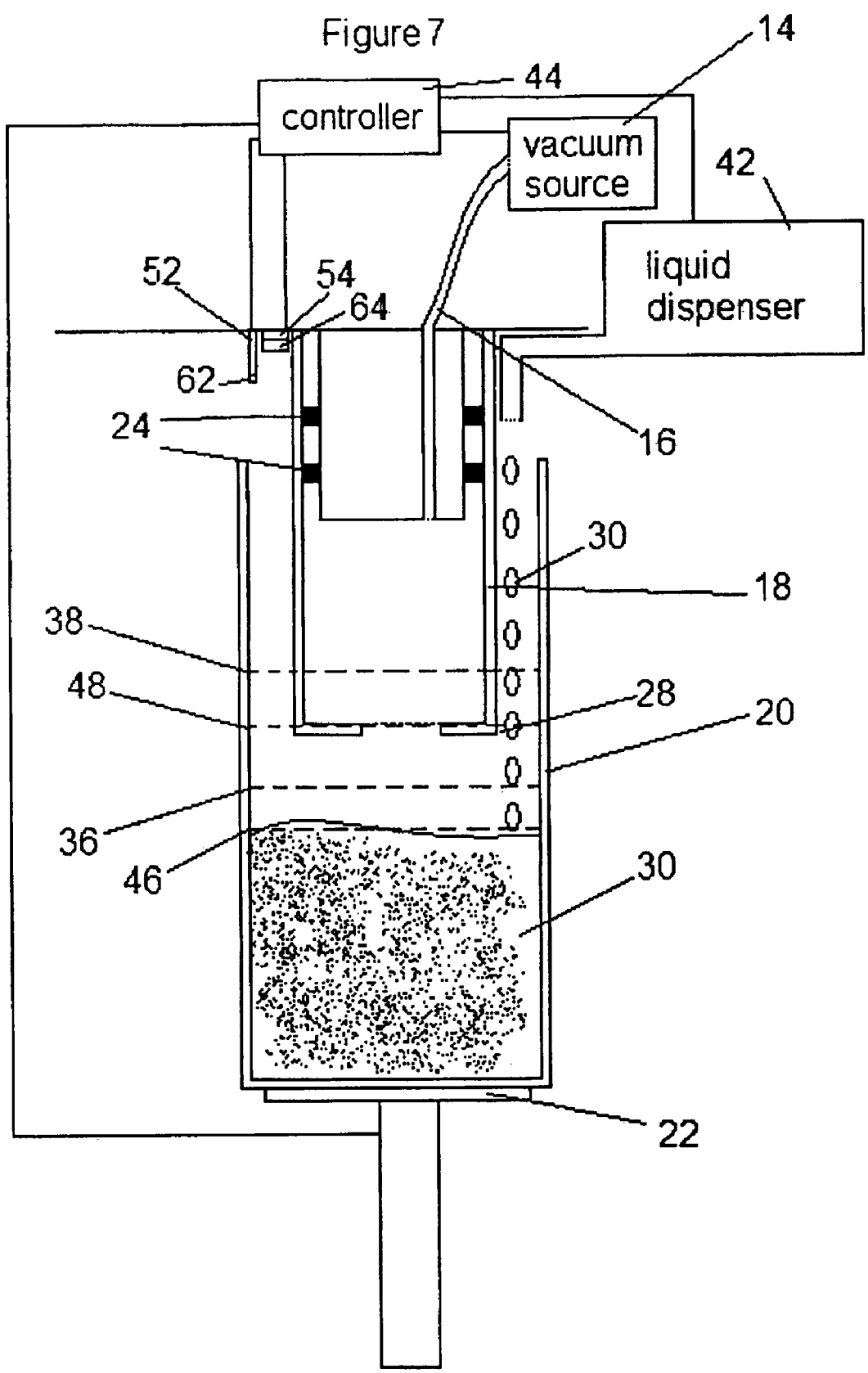

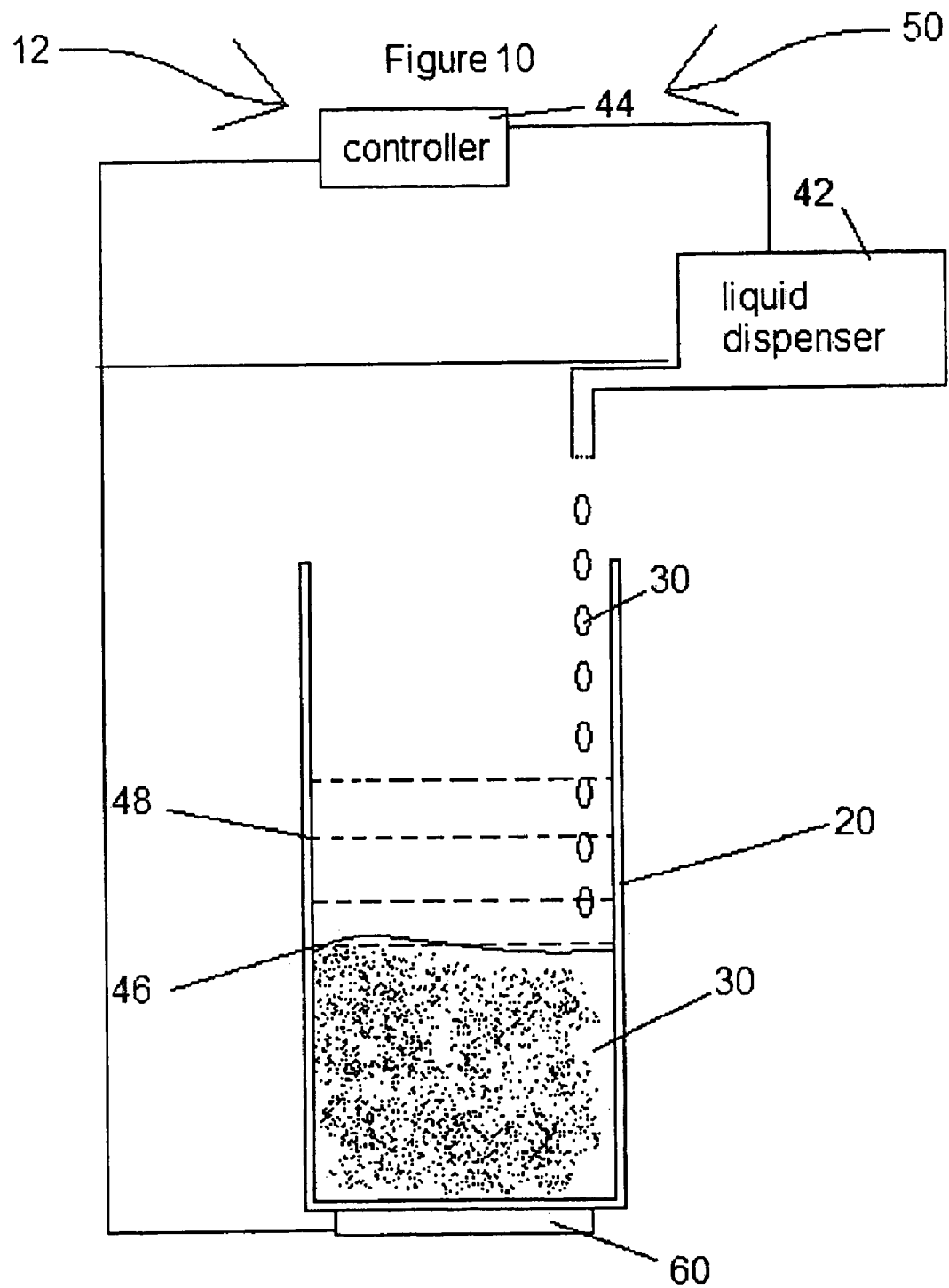

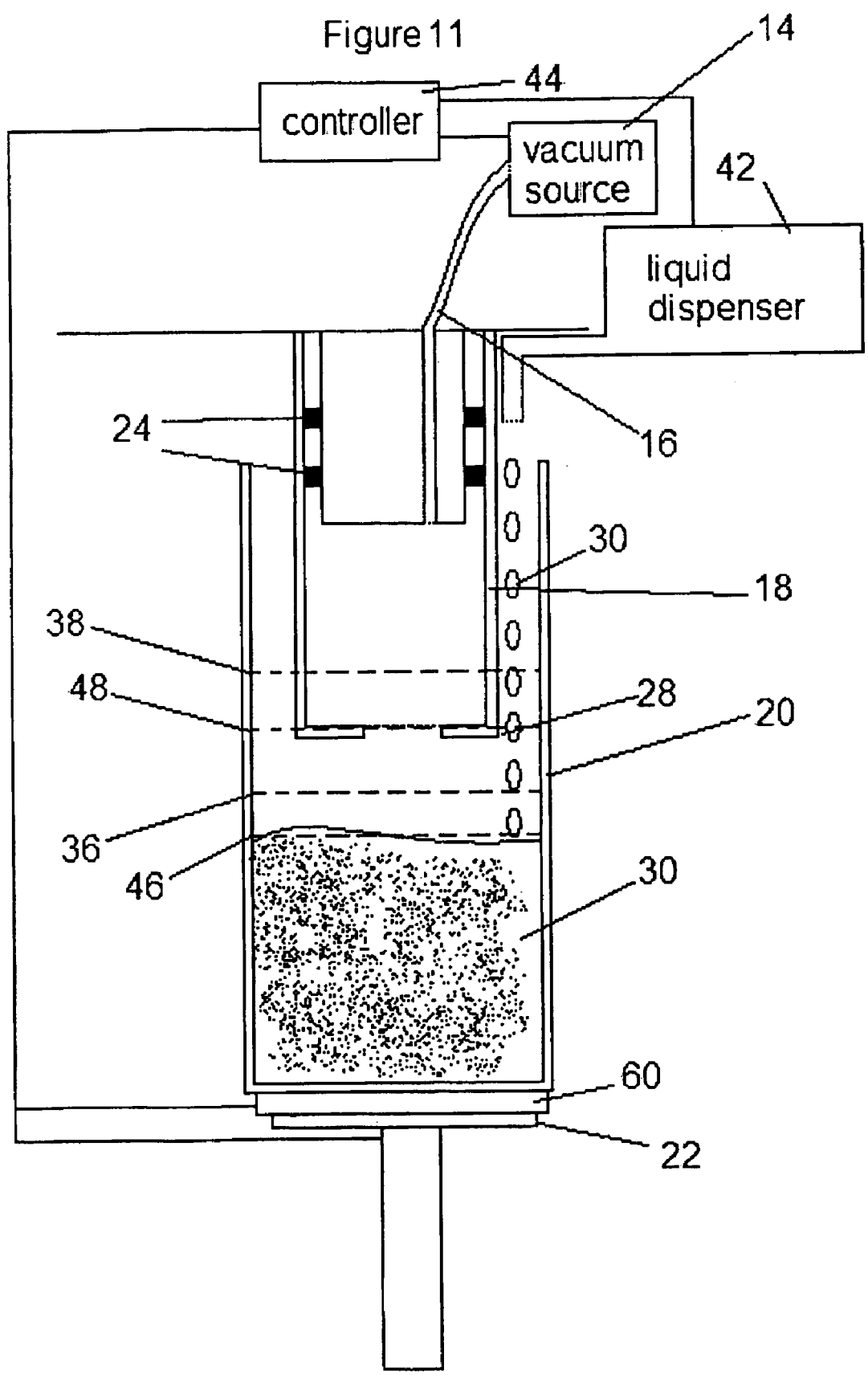

FLUID LEVEL REGULATOR

FIELD OF INVENTION

The present invention generally relates to systems for preparing biological specimens, and more particularly, to devices for automatically monitoring and adjusting the fluid level in biological sample containers.

DESCRIPTION OF RELATED ART

Many medical diagnostic tests, such as pap smears, require a physician to collect cells by brushing and/or scraping a skin or mucous membrane in a target area with an instrument. The collected cells are typically smeared ("fixed") onto a slide, and stained to facilitate examination under a microscope by a cytotechnologist and/or pathologist. For example, a pathologist may employ a polychrome technique, characterized by staining the nuclear part of the cells, to determine the presence of dysplasia or neoplasia. The pathologist may also apply a counter-stain for viewing the cytoplasm of the cells. Because the sample may contain debris, blood, mucus and other obscuring artifacts, the test may be difficult to evaluate, and may not provide an accurate diagnostic assessment of the collected sample.

Cytology based on the collection of the exfoliated cells into a fluid preservative offers many advantages over the traditional method of smearing the cells directly onto the slide. A slide can be prepared from the cell suspension using a filter transfer technique, as disclosed in U.S. Pat. Nos. 6,572,824, 6,318,190, 5,772,818, 5,364,597 and 5,143,627, which are expressly incorporated herein by reference.

Filter transfer methods generally start with a collection of cells suspended in a fluid. These cells may be collected and dispersed into a fluid preservative or they may naturally exist in a collected biological fluid. Dispersion in fluid preservatives containing methanol, such as PreservCyt™ solution, breaks up mucus and lyses red blood cells and inflammatory cells, without affecting the cells of interest. The fluid is passed through a filter with a fixed diameter aperture covered by a membrane to concentrate and collect the cells. Debris, such as lysed blood cells and dispersed mucus, which flow through the pores of the membrane, are not collected on the membrane and are greatly reduced in the collected specimen by the combined methods of dispersion and filtering. Then the cells collected on the membrane are transferred onto a slide for further processing, such as visual examination.

Filter transfer methods use a vacuum source to draw the cell containing fluid across the membrane and into a filter cartridge. The vacuum source is only able to draw fluid if the filter transfer apparatus positions the membrane end of the filter cartridge into the fluid in the container. Therefore, in order to automate filter cartridge and fluid container handling in a filter transfer method, the height of the fluid, and therefore the amount of fluid, in a container is preferably within a standardized range.

When the vacuum source is activated, the pressure inside the filter cartridge is temporarily lowered. Filter transfer apparatuses use the "decay" of this temporary pressure drop (the time elapsed before the pressure returns to atmospheric pressure) to derive the amount of cells collected on the membrane of the filter. It has been found that the height of the fluid in the container affects the decay time of the pressure drop, as well as the amount of negative pressure needed to draw the fluid into the filter and the amount of positive pressure needed to expel the fluid from the filter (in a membrane pre-wetting step). These effects become more pronounced when smaller amounts of fluid are used, such as with DNA analysis (vs. traditional visualization).

Existing filter transfer methods use a frosted band and manual inspection to keep the amount of fluid in a container within a standardized range. In addition to taking up valuable laboratory technician time, manually processing large numbers of samples can potentially lead to errors because of human involvement in the inspection and handling of samples. Such errors could include misreading the fluid level and contamination of samples. Misreading the fluid level can lead to faults in the filter transfer apparatus, decreasing throughput of the machines while faults are remedied.

Contamination has at least two consequences. First, some biological samples are very inconvenient, if not impossible, to re-harvest. While it is highly inconvenient for a patient to repeat a pap smear, it is may not be possible to repeat a biopsy on a mole that has been removed to test for malignancy. Second, for those situations where a second sample collection is not a viable option, chain of custody issues can have serious repercussions. Such chain of custody issues can call into doubt entire batches of test results and, in the worst cases, all results from a clinical lab.

SUMMARY OF THE INVENTION

In some embodiments, a biological specimen collection and transfer system, comprises a biological sample container configured for storing a biological fluid sample, and a fluid level regulator configured to determine a fluid level in the biological sample container and to dispense a fluid into the container if the determined fluid level is less than a desired fluid level. The system may also include a filtration based biological specimen slide processor. The fluid level regulator comprises a fluid level monitor, a fluid dispenser, and a controller in communication with the fluid level monitor and the fluid dispenser.

In some embodiments, the system also includes a vacuum source, a specimen filter having an interior chamber and an opening in communication with the chamber, a vacuum conduit configured to couple the vacuum source to the specimen filter chamber, and a pressure sensor configured to measure a pressure in the specimen filter chamber while the chamber is coupled with the vacuum source and the opening is submerged in the fluid sample, wherein the controller determines the fluid level based at least in part on the measured pressure. The system may also include an elevator for moving the sample container relative to the specimen filter, wherein the controller determines the fluid level in further part based on a relative position of the elevator.

In some embodiments, the fluid level monitor comprises a light source configured to emit light towards a surface of the fluid sample, and a light detector configured to measure light reflected from the surface of the fluid sample, wherein the controller determines the fluid level based at least in part on a measurement of reflected light emitted from the light source.

In some embodiments, the fluid sample container is translucent and the fluid level monitor comprises a light source configured to emit light towards a side of the fluid sample container, and a light detector configured to measure light passing through the fluid sample container, wherein the controller determines the fluid level based at least in part on a measurement of detected light emitted from the light source.

In some embodiments, the fluid level monitor comprises a sound source configured to emit sound towards a surface of the fluid sample, and a sound detector configured to measure sound reflected from the surface of the fluid sample, wherein the controller determines the fluid level based at least in part on a measurement of reflected sound emitted from the sound source.

In some embodiments, the fluid level monitor comprising a scale, wherein the controller determines the fluid level based at least in part of a measured weight of the fluid sample container including the fluid sample In some embodiments, a method of regulating a fluid level of a biological fluid sample in a container during a process of transferring biological matter in the fluid sample to a specimen slide, the method comprises monitoring a pressure of an interior chamber of a specimen filter, the chamber coupled to a vacuum source and having one end submerged in the fluid sample, determining a fluid level of the fluid sample in the container based on a detected change in pressure of the specimen filter chamber, and adding a liquid to the container if the determined fluid level is less than a desired fluid level.

In some embodiments, a method of regulating a fluid level of a biological fluid sample in a container during a process of transferring biological matter in the fluid sample to a specimen slide, the method comprises emitting light into the container, measuring an amount of light emitted into the container and reflected by the fluid sample, determining a fluid level based on the measured reflected light, and adding a liquid to the container if the determined fluid level is less than a desired fluid level.

BRIEF DESCRIPTION OF THE DRAWINGS

In order to better understand and appreciate the invention, reference should be made to the drawings and accompany detailed description, which illustrate and describe exemplary embodiments thereof. For ease in illustration and understanding, similar elements in the different illustrated embodiments are referred to by common reference numerals. In particular:

FIG. 4A is a schematic view of the exemplary filter/container interface of FIG. 3;

FIG. 4B is a schematic view of the exemplary filter/container interface of FIG. 3;

FIG. 5 is a schematic view of the exemplary filter/container interface of FIG. 3;

FIG. 6 is a schematic view of an exemplary fluid regulation station of a biological specimen collection and transfer system according to another embodiment of the invention;

FIG. 7 is a schematic view of an exemplary filter/container interface of a biological specimen collection and transfer system according to another embodiment of the invention;

FIG. 10 is a schematic view of an exemplary fluid regulation station of a biological specimen collection and transfer system according to another embodiment of the invention; and FIG. 11 is a schematic view of an exemplary filter/container interface of a biological specimen collection and transfer system according to another embodiment of the invention.

DETAILED DESCRIPTION OF THE ILLUSTRATED EMBODIMENTS

In the following description of the illustrated embodiments, it will be understood by those skilled in the art that the drawings and specific components thereof are not necessarily to scale, and that various structural changes may be made without departing from the scope or nature of the various embodiments.

Figure 1:
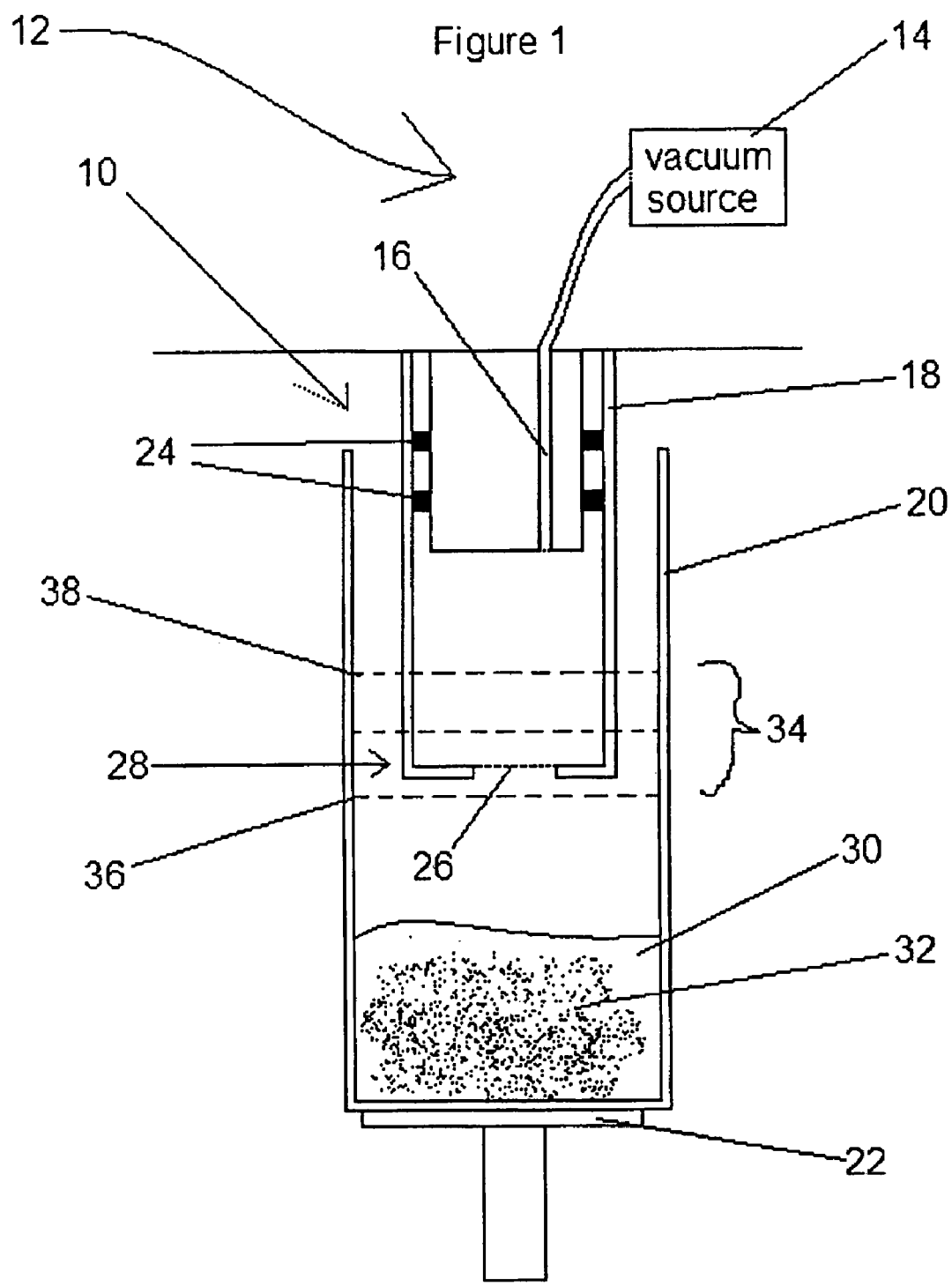
FIG. 1 is a schematic view of an exemplary filter/container interface of a biological specimen collection and transfer system.

Referring to FIG. 1, a filter/container interface 10 of a biological specimen collection and transfer system 12 is shown. In this embodiment, the filter/container interface 10 includes a vacuum source 14, a vacuum conduit 16, a filter cartridge 18, a sample container 20, and an elevator 22. The vacuum conduit 16 is connected, with air tight seals 24, to the vacuum source 14 and the filter cartridge 18. The filter cartridge 18 has a membrane 26 at an open distal end 28, which is configured to be submerged into a fluid 30 containing a biological specimen 32, such as collected cervical cells. The sample container 20 holds the fluid 30 and the elevator 22 moves the sample container 20 relative to the filter cartridge 18. Alternatively, the sample container 20 can be stationary and the filter cartridge 18 can be movable.

Figure 2:
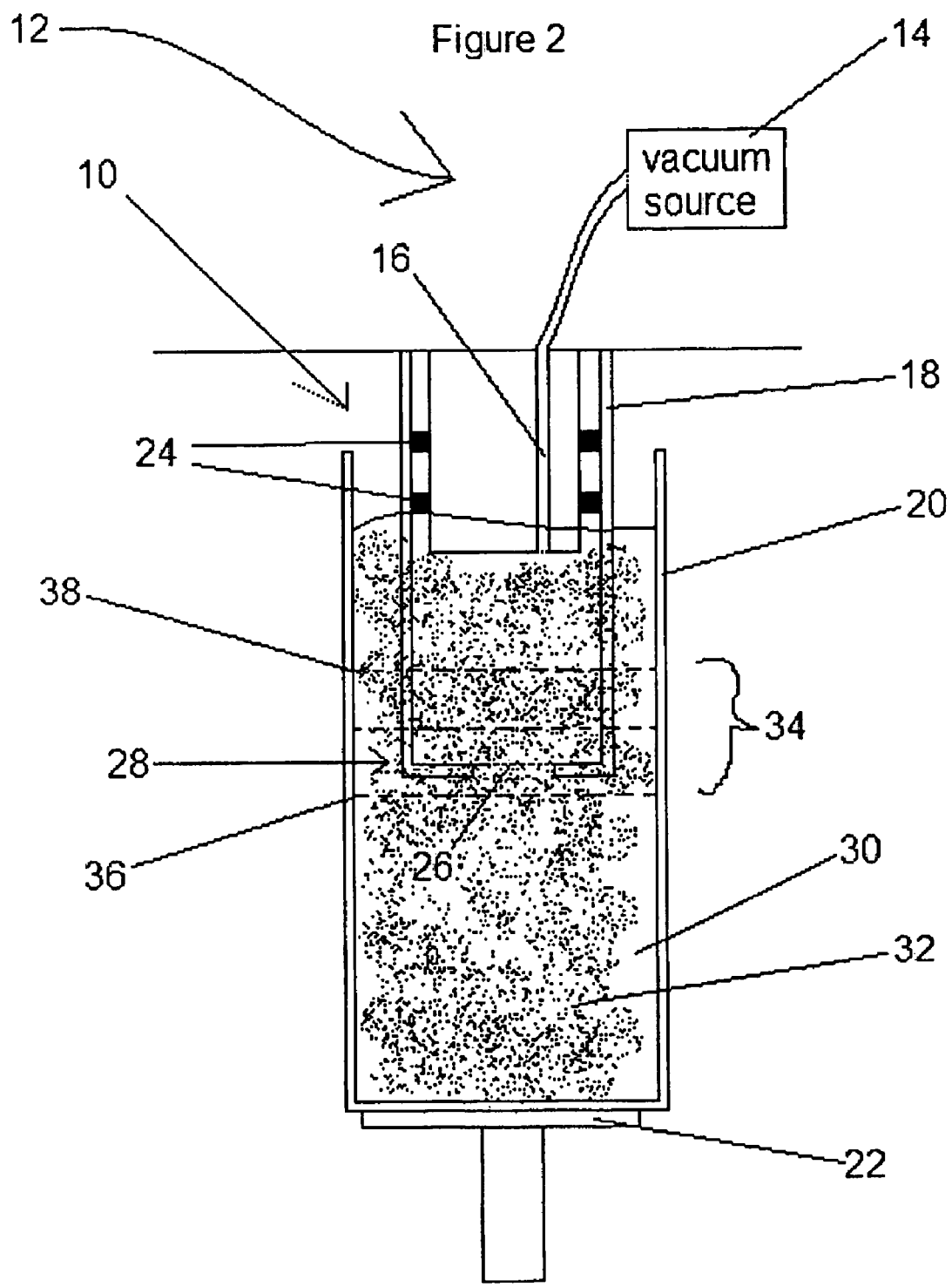
FIG. 2 is the schematic view of another exemplary filter/container interface of FIG. 1.

The sample container 20 has a frosted band 34, which indicates a minimum fluid level 36 and a maximum fluid level 38 for the collection and transfer system 12 to function properly. If there is less than the minimum level 36 of fluid 30, as shown in FIG. 1, the distal end 28 of the filter cartridge 18 will be exposed to air during collection of the biological specimen 32. Exposure to air interferes with collection and transfer by prematurely interrupting the collection process and drying the collected biological specimen 32. If there is more than the maximum level 38 of fluid 30, as shown in FIG. 2, the fluid 30 will overflow out of the container 20 as the filter cartridge 18 is inserted into the container 20 during the collection and transfer process. The overflowing fluid 30 can contaminate the collection and transfer system 12, the filter/container interface 10, and all subsequently processed containers 20 and filter cartridges 18.

Figure 3:
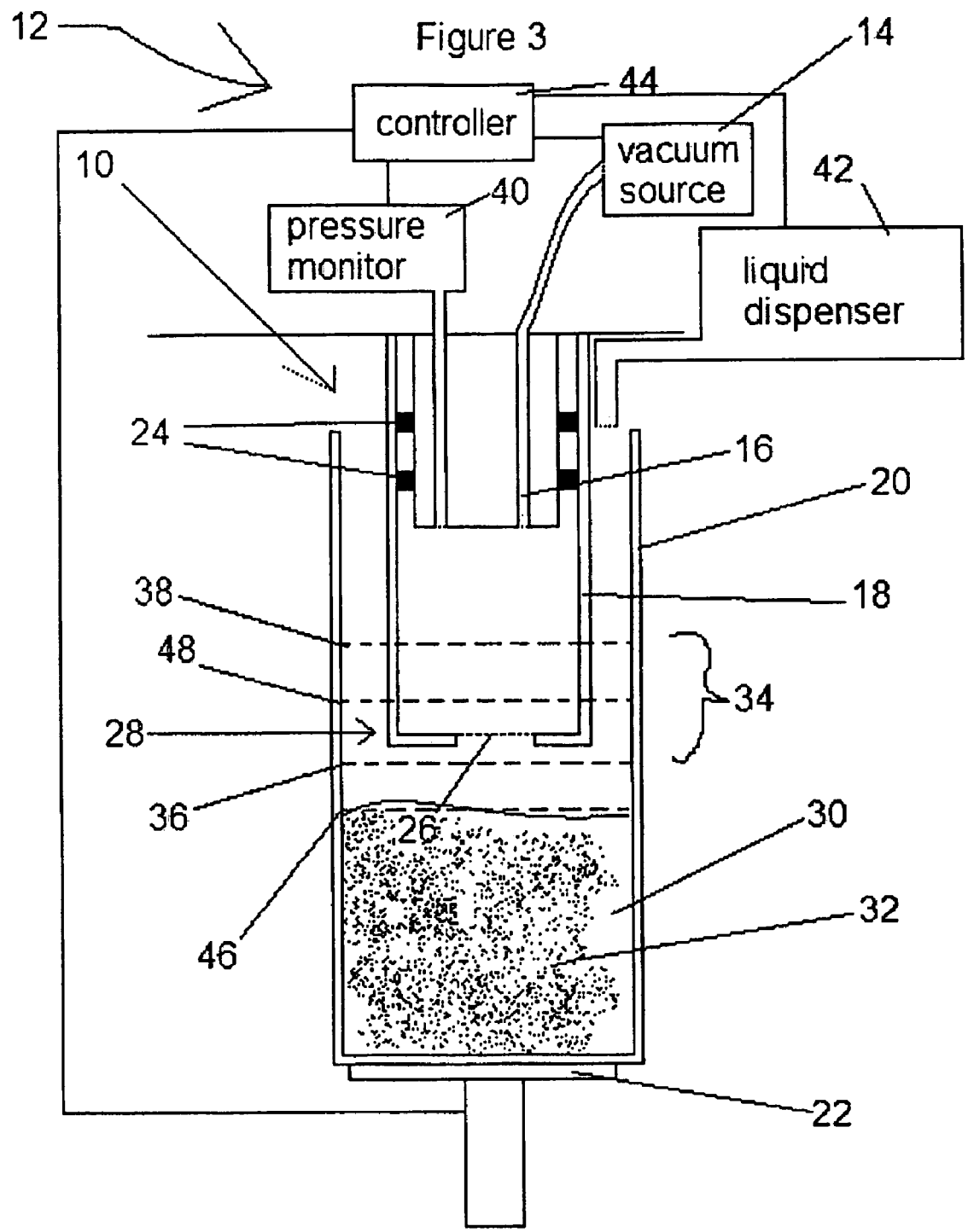
FIG. 3 is a schematic view of an exemplary filter/container interface of a biological specimen collection and transfer system according to one embodiment of the invention.

Referring to FIG. 3, another biological specimen collection and transfer system 12 is shown. The biological specimen collection and transfer system 12 generally includes a biological specimen slide processor (not shown) and the filter/container interface 10. In this embodiment, the filter/container interface 10 includes the vacuum source 14, the vacuum conduit 16, the filter cartridge 18, the sample container 20, the elevator 22, a pressure sensor 40, a fluid dispenser 42 and a controller 44. The pressure sensor 40 is configured to accurately measure the pressure inside of the filter cartridge 18. The controller 44 uses information from the pressure sensor 40 and the elevator 22 to determine a fluid level 46 in the sample container 20.

During the biological specimen collection and transfer process, the distal end 28 of the filter cartridge 18 is positioned just inside of the sample container 20, as shown in FIG. 4A. The vacuum source 14 is activated and the vacuum that it generates is conveyed by the vacuum conduit 16 to the filter cartridge 18. Further, the pressure sensor 40 is activated. Because the inside of the filter cartridge 18 is open at the distal end 28, the pressure sensor 40 reads atmospheric pressure.

Then the elevator 22 raises the sample container 20, moving distal end 28 of the filter cartridge 18 closer to the fluid 30 in the sample container 20, as shown in FIG. 4B. When the distal end 28 of the filter cartridge 18 touches the fluid 30 in the sample container 20, the fluid 30 closes the distal end 28 of the filter cartridge 18 and the pressure inside of the filter cartridge 18 drops precipitously. In this way, the filter cartridge 18 acts as a probe for the fluid 30 in the sample container 20. The controller 44 is configured to note this pressure drop and to use the position of the elevator 22 at the time of the pressure drop and known parameters, such as the starting positions of the filter cartridge 18 and the sample container 20, and the dimensions of the sample container 20, to derive the height and amount of fluid 30 in the sample container 20.

Figure 4C:
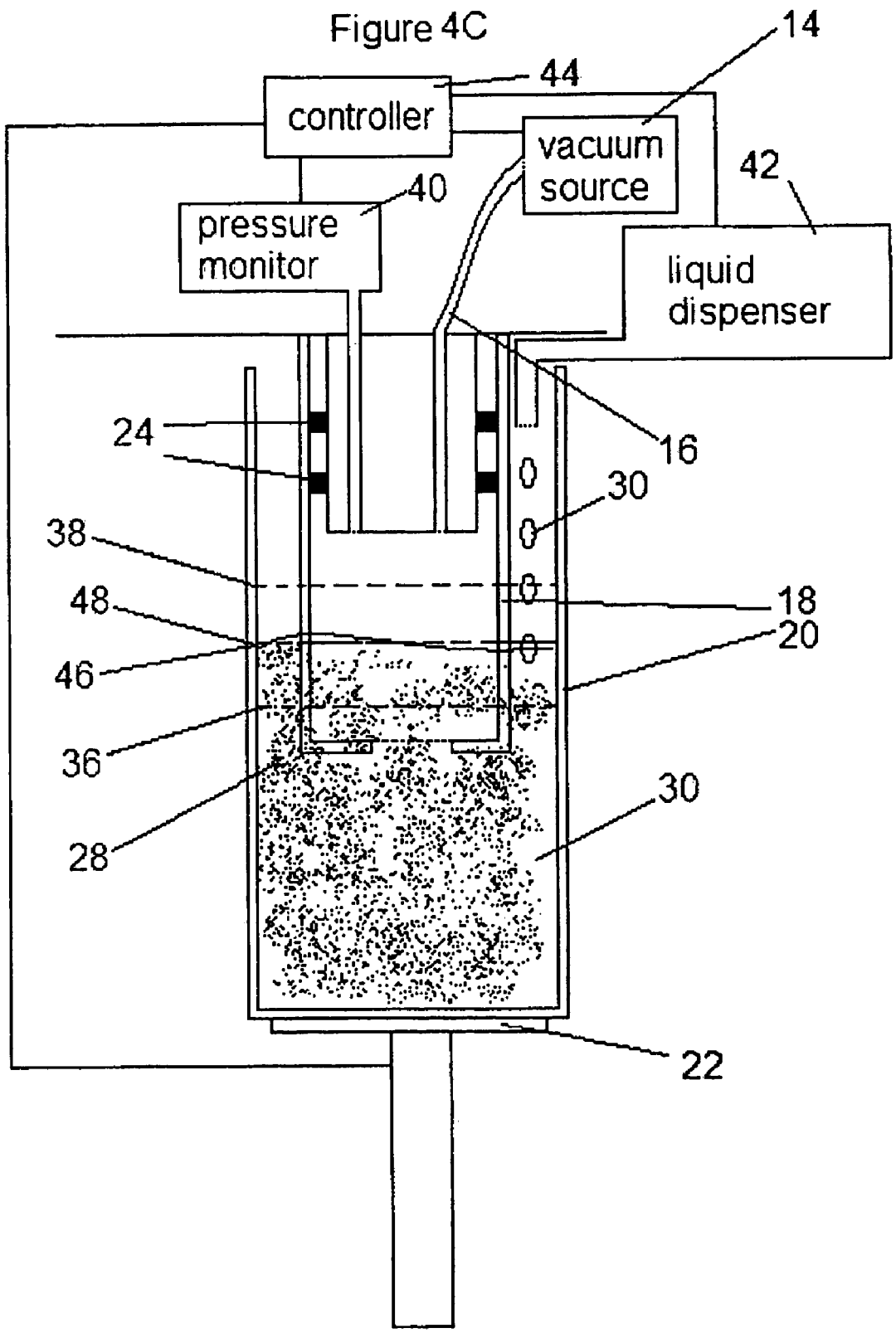
FIG. 4C is a schematic view of the exemplary filter/container interface of FIG. 3.

The controller 44 then derives the amount of fluid 30 needed to bring the fluid level 46 to an optimal level 48 between the minimum level 36 and the maximum level 38. The fluid dispenser 42 then metes out the derived amount of fluid 30, which does not contain any biological specimens 32, as shown in FIG. 4C. After the fluid level 46 is adjusted, the position of the elevator 22 can be reset and the pressure sensor 40 can be used, as described above, to confirm the fluid level 46.

Alternatively, as shown in FIG. 5, the elevator 22 can position the sample container 20 so that the distal end 28 of the filter cartridge 18 is located at the optimal level 48. Then the fluid dispenser 42 metes out fluid 30 until the pressure sensor 40 detects a pressure drop inside of the filter cartridge 18. This pressure drop coincides with the fluid level 46 reaching the optimal level 48.

FIG. 6 shows an alternative embodiment wherein the biological specimen collection and transfer system 12 comprises a fluid level station 50. The fluid level station 50 contains the sample container 20, the fluid dispenser 42, the controller 44, a light source 52 and a light sensor 54. The light source 52 and the light sensor 54 are located above the sample container 20 and directed into it. The light source 52 sends light into the sample container 20, which reflects off the fluid 30 in the sample container 20 and is detected by the light sensor 54. Using the data from the light sensor 54 and known methods, the controller 44 derives the distance to the fluid 30. Using this distance and known parameters about the fluid level station 50, the controller 44 extrapolates the height of the fluid 30 and the amount of fluid 30 in the sample container 20, and determines the amount of fluid 30 needed to bring the fluid level 46 to the optimal level 48. The fluid dispenser 42 then metes out the derived amount of fluid 30. Then the light source 52 and light sensor 54 can be used, as described above, to verify the fluid level 46. The light source 52 comprises a cover 62, configured to close the light source 52 and prevent contamination by splashing fluid 30. The light sensor 54 comprise a wiper 64, configured to clean the light sensor 54. The cover 62 and wiper 64 can be used interchangeably with the light source 52 and light sensor 54.

Figure 8:
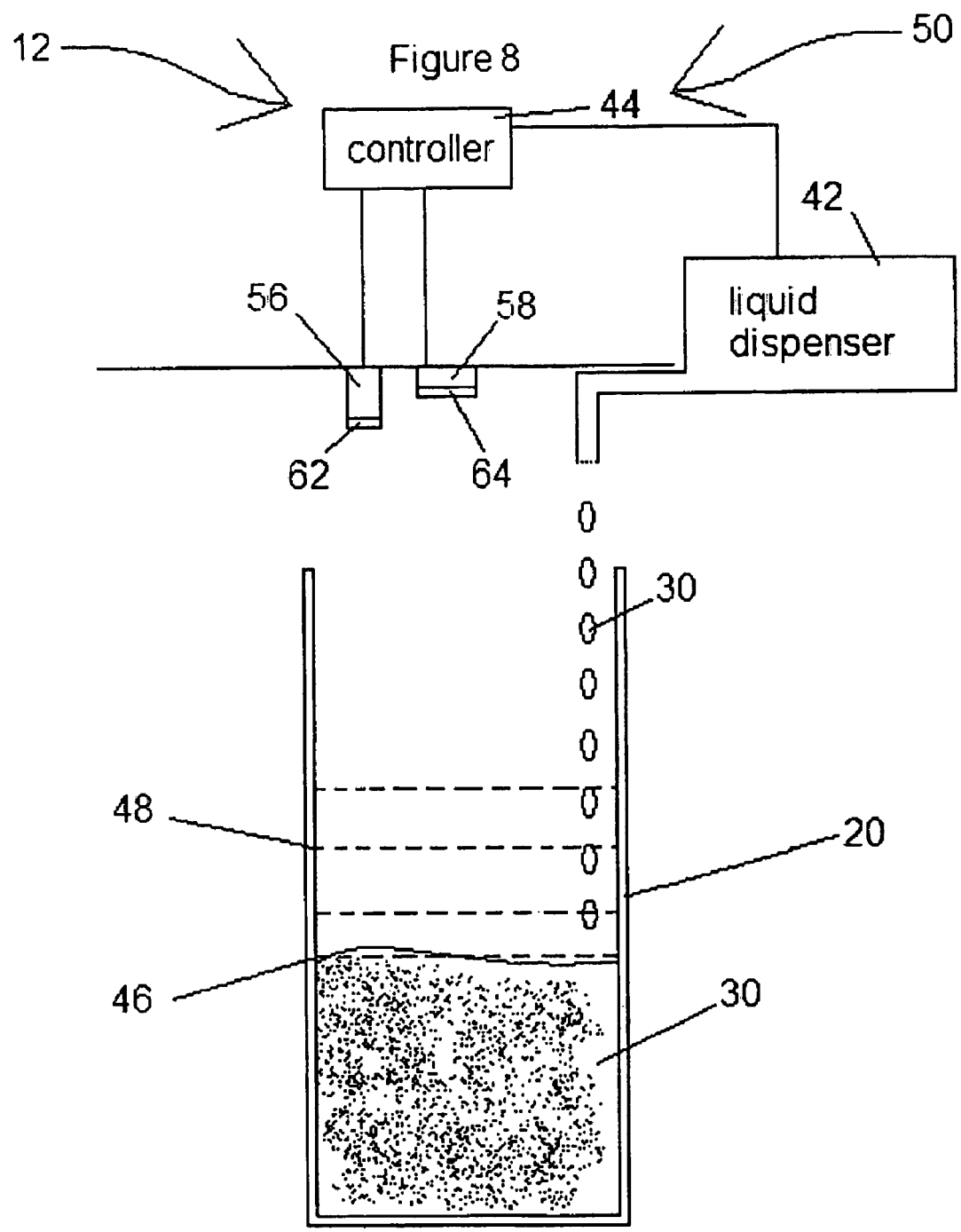
FIG. 8 is a schematic view of an exemplary fluid regulation station of a biological specimen collection and transfer system according to another embodiment of the invention.

In an alternative embodiment, as shown in FIG. 7, the fluid dispenser 42, the controller 44, the light source 52 and the light sensor 54 can be incorporated into the filter/container interface 10, but function as in the embodiment with the separate fluid level station 50. In yet another alternative embodiment, as shown in FIG. 8, the light source 52 and light sensor 54 are replaced with a sound source 56 and a sound detector 58, but function as in the embodiment using light. Covers 62 and wipers 64 can also be used with these embodiments.

Figure 9:
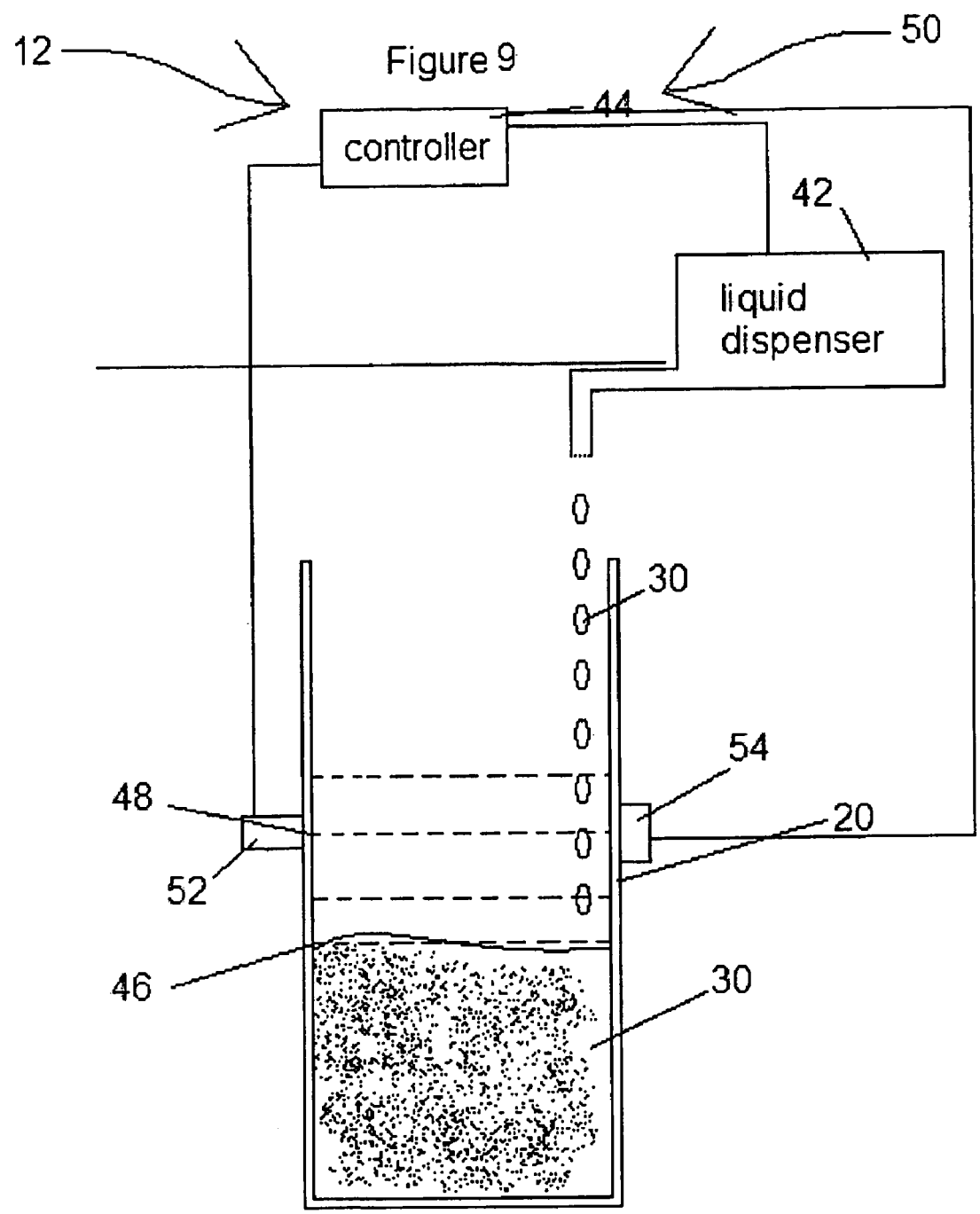
FIG. 9 is a schematic view of an exemplary fluid regulation station of a biological specimen collection and transfer system according to another embodiment of the invention.

In still another alternative embodiment, as shown in FIG. 9, the light source 52 and light sensor 54 are located across from each other along the line approximating the optimal fluid level 48. The controller 44 in this embodiment, uses the change in transmitted light with intervening fluid 30 to first confirm that the amount of fluid 30 in the sample container 20 is below the minimum fluid level 36. Then the fluid dispenser 42 metes out fluid 30 until the light sensor 54 detects a change in the transmitted light, signifying that the level of fluid 30 has reached the optimal level 48.

FIG. 10 shows an alternative embodiment wherein the fluid level station 50 includes the sample container 20, the fluid dispenser 42, the controller 44 and a scale 60. The scale 60 is calibrated with an empty sample container 20 and weighs the fluid 30 in a sample container 20 to be processed. The controller 44 uses the weight of the fluid 30 to derive the amount and height of fluid 30 in the sample container 20, and determines the amount of fluid 30 needed to bring the fluid level 46 to the optimal level 48. The fluid dispenser 42 then metes out the derived amount of fluid 30. Then the scale 60 can reweigh the fluid 30 in the sample container 20 to verify the fluid level 46.

In an alternative embodiment, as shown in FIG. 11, the fluid dispenser 42, the controller 44 and the scale 60 can be incorporated into the filter/container interface 10, but function as in the embodiment with the separate fluid level station 50.

Although various embodiments of the invention have been shown and described herein, it should be understood that the above description and figures are for purposes of illustration only, and are not intended to be limiting of the invention, which is defined only by the appended claims and their equivalents.

What is claimed:

1. A biological specimen collection and transfer system, comprising:
    a biological sample container configured for storing a biological fluid sample;
    a vacuum source;
    a specimen filter having an interior chamber and an opening in communication with the chamber; and
    a fluid level regulator configured to determine a fluid level in the biological sample container and to dispense a fluid into the container if the determined fluid level is less than a desired fluid level, wherein the fluid level regulator comprises:
        a fluid level monitor;
        a fluid dispenser; and
        a controller in communication with the fluid level monitor and the fluid dispenser,
        wherein the fluid level monitor comprises a pressure sensor configured to measure a pressure in the specimen filter chamber while the chamber is coupled with the vacuum source and the opening is submerged in the fluid sample, wherein the controller uses the measured pressure in determining the fluid level.

2. The system of claim 1, further comprising a filtration based biological specimen slide processor.

3. The system of claim 1, further comprising
    a vacuum conduit configured to couple the vacuum source to the specimen filter chamber.

4. The system of claim 1, further comprising an elevator for moving the sample container relative to the specimen filter, wherein the controller uses a relative position of the elevator in determining the fluid level.

5. The system of claim 1, wherein the opening in the specimen filter is positioned at the desired fluid level.

6. A biological specimen collection and transfer system, comprising:
    a biological sample container configured for storing a biological fluid sample, the fluid sample container being translucent;

a fluid level regulator configured to determine a fluid level in the biological sample container and to dispense a fluid into the container if the determined fluid level is less than a desired fluid level, wherein the fluid level regulator comprises:

a fluid level monitor;

a fluid dispenser; and a controller in communication with the fluid level monitor and the fluid dispenser, wherein the fluid level monitor comprises a light source configured to emit light towards a side of the fluid sample container; and a light detector configured to measure light passing through the fluid sample container, wherein the controller uses a measurement of detected light emitted from the light source in determining the fluid level.

7. The system of claim 6, further comprising a filtration based biological specimen slide processor.

8. A method of regulating a fluid level of a biological fluid sample in a container during a process of transferring biological matter in the fluid sample to a specimen slide, the method comprising:

monitoring a pressure of an interior chamber of a specimen filter, the chamber coupled to a vacuum source and having one end submerged in the fluid sample;

determining a fluid level of the fluid sample in the container based on a detected change in pressure of the specimen filter chamber;

adding a liquid to the container if the determined fluid level is less than a desired fluid level; and submerging the one end of the chamber by moving the container towards the one end of the chamber until the change in pressure is detected.

9. A method of regulating a fluid level of a biological fluid sample in a container during a process of transferring biological matter in the fluid sample to a specimen slide, the method comprising:

monitoring a pressure of an interior chamber of a specimen filter, the chamber coupled to a vacuum source and having one end submerged in the fluid sample;

determining a fluid level of the fluid sample in the container based on a detected change in pressure of the specimen filter chamber;

adding a liquid to the container if the determined fluid level is less than a desired fluid level; and submerging the one end of the chamber by disposing the one end of the chamber at the desired fluid level and adding the liquid to the container until the change in pressure is detected and the determined fluid level is equal to the desired fluid level.

* * * * *